US011045175B2

(12) United States Patent
Coelho, Jr. et al.

(10) Patent No.: US 11,045,175 B2
(45) Date of Patent: Jun. 29, 2021

(54) SURGICAL DEVICE FOR USE WITH ROBOTIC SURGICAL SYSTEMS

(71) Applicant: C.R. Bard, Inc., Murray Hill, NJ (US)

(72) Inventors: Donald A. Coelho, Jr., Bellingham, MA (US); John Conidi, Plainville, MA (US); Peter Maughan Crapo, North Kingstown, RI (US); Augustus Felix, Cranston, RI (US); Ian K. Parker, Bristol, RI (US); Devang Vijay Shah, Franklin, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 93 days.

(21) Appl. No.: 15/676,834

(22) Filed: Aug. 14, 2017

(65) Prior Publication Data
US 2019/0046172 A1    Feb. 14, 2019

(51) Int. Cl.
*A61B 34/30* (2016.01)
*A61B 17/068* (2006.01)
(Continued)

(52) U.S. Cl.
CPC .... *A61B 17/00234* (2013.01); *A61B 17/0469* (2013.01); *A61B 17/068* (2013.01); *A61B 34/30* (2016.02); *A61B 17/064* (2013.01); *A61B 17/0642* (2013.01); *A61B 17/92* (2013.01); *A61B 2017/00402* (2013.01); *A61B 2017/00407* (2013.01); *A61B 2017/00477* (2013.01); *A61B 2017/0647* (2013.01);
(Continued)

(58) Field of Classification Search
CPC .......... A61B 34/30; A61B 2017/00477; A61B 17/068
See application file for complete search history.

(56) References Cited

U.S. PATENT DOCUMENTS 6,231,565 B1    5/2001  Tovey et al.
2001/0037109 A1*  11/2001  Yamauchi .......... A61B 18/1445
                                                    606/48
(Continued)

FOREIGN PATENT DOCUMENTS

WO    WO 2013/068978 A1    5/2013

OTHER PUBLICATIONS

International Search Report and Written Opinion for International Application No. PCT/US2018/044789, dated Oct. 31, 2018.

*Primary Examiner* — William J Levicky
(74) *Attorney, Agent, or Firm* — Wolf, Greenfield & Sacks, P.C.

(57) ABSTRACT

Surgical devices for use with robotic surgical systems and their methods of use are described. In some embodiments, the surgical device may include an actuator that interfaces with an end effector of an arm of a robotic surgical system. An output from the end effector may actuate the actuator to perform an operation of the surgical device. In some embodiments, the surgical device may include a retainer that retains at least a portion of the surgical device on a distal portion of the arm of the robotic surgical system during actuation. In other embodiments, the surgical device may include a portion that is engaged by a second robotic surgical arm to hold at least a portion of the surgical device stationary relative to the robotic surgical arm engaged with the actuator of the surgical device.

37 Claims, 7 Drawing Sheets

(51) Int. Cl.
*A61B 17/00* (2006.01)
*A61B 17/04* (2006.01)
A61B 17/064 (2006.01)
A61B 17/92 (2006.01)

(52) U.S. Cl.
CPC .......... *A61B 2017/0648* (2013.01); *A61B 2017/0649* (2013.01); *A61B 2017/925* (2013.01)

(56) References Cited

U.S. PATENT DOCUMENTS

| | | | |
|---|---|---|---|
| 2008/0243141 A1* | 10/2008 | Privitera | A61B 18/1445 606/130 |
| 2011/0288573 A1 | 11/2011 | Yates et al. | |
| 2012/0323256 A1* | 12/2012 | Privitera | A61B 18/1445 606/130 |
| 2013/0310813 A1* | 11/2013 | Kaercher | A61B 17/00 606/1 |
| 2016/0287445 A1* | 10/2016 | Wasicek | A61B 18/1492 |
| 2018/0036007 A1* | 2/2018 | Fago | A61B 17/1285 |
| 2018/0221102 A1* | 8/2018 | Wang | A61B 34/30 |
| 2018/0256241 A1* | 9/2018 | Cohen | A61B 18/1445 |

\* cited by examiner

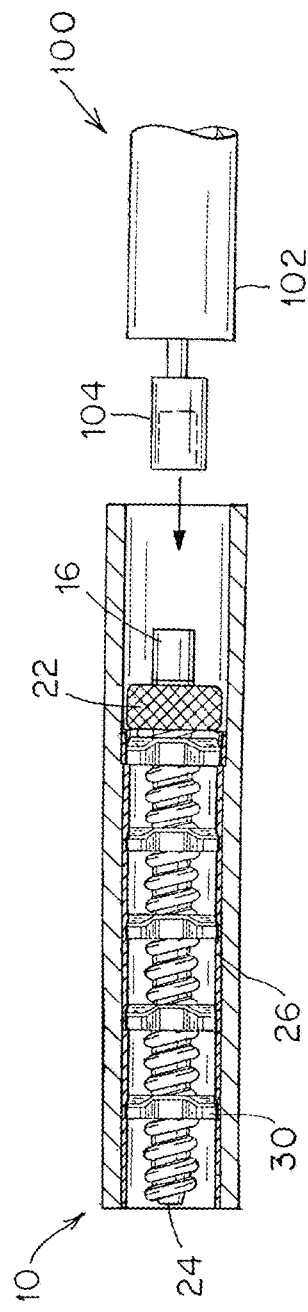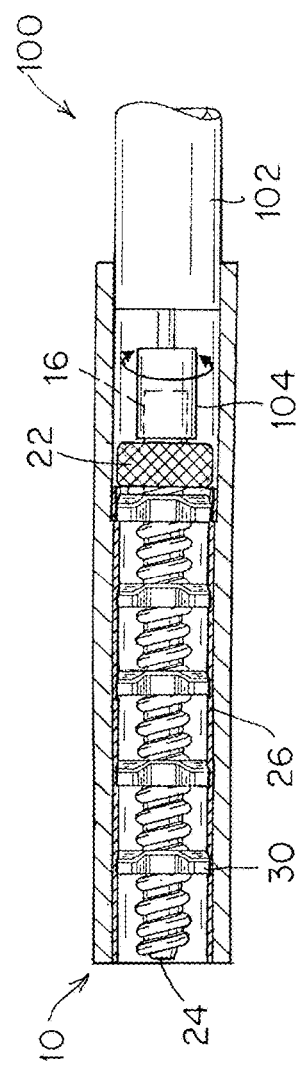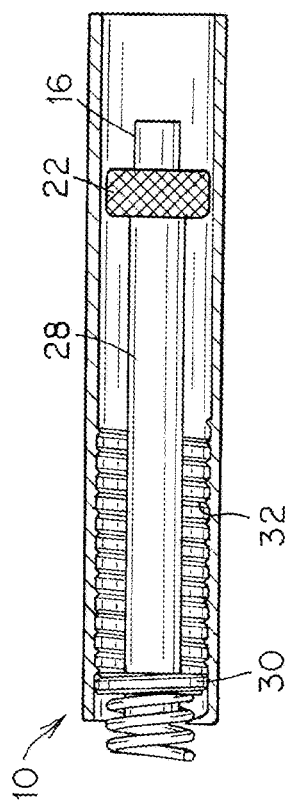

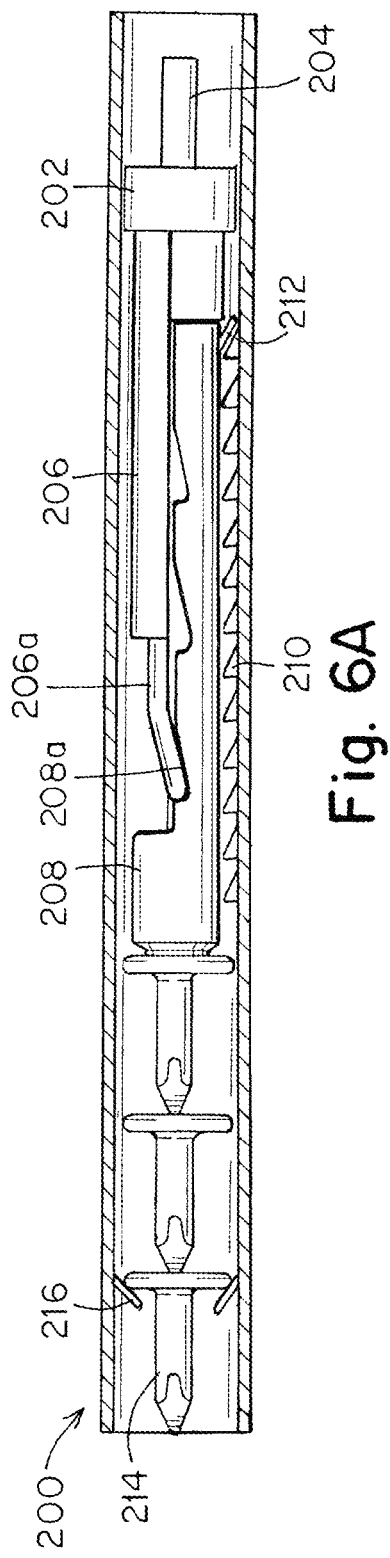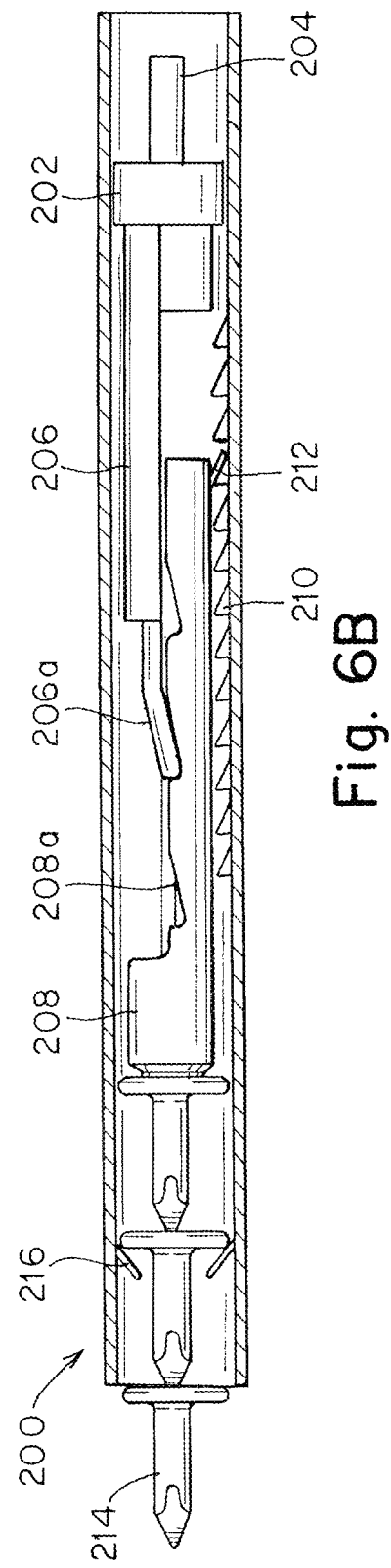

SURGICAL DEVICE FOR USE WITH ROBOTIC SURGICAL SYSTEMS

FIELD

Disclosed embodiments are related to surgical devices for use with robotic surgical systems.

BACKGROUND

Minimally invasive surgery is commonly performed on a localized part of a body. Such surgery may be performed manually or by robotic surgical systems. During some types of operations, surgical devices and/or arms of a robotic surgical system may be inserted into the body through a trocar that is placed within an incision or orifice. The surgeon may then operate the surgical devices and/or robotic surgical system to perform a desired operation on a subject's body.

SUMMARY

In one embodiment, a surgical device for use with a robotic surgical system includes: a housing and an actuator adapted to interface with an end effector of an arm of the robotic surgical system such that an output from the end effector of the arm of the robotic surgical system actuates the actuator. The actuator is supported by the housing. The surgical device also includes a retainer adapted to retain at least a portion of the housing on a distal portion of the arm of the robotic surgical system during actuation of the actuator.

In another embodiment, a surgical device for use with a robotic surgical system includes a housing and an actuator adapted to interface with a first end effector of a first arm of the robotic surgical system such that an output from the end effector of the first arm of the robotic surgical system actuates the actuator. The actuator is supported by the housing and at least a portion of the surgical device is adapted to be retained by a second end effector of a second arm of the robotic surgical system to hold at least a portion of the surgical device at least one of rotationally and longitudinally stationary relative to the first arm.

In yet another embodiment, a method of operating a surgical device with a robotic surgical system includes: securing at least a portion of a housing of the surgical device on a distal end of an arm of the robotic surgical system; engaging an actuator of the surgical device with an end effector of the arm of the robotic surgical system; and actuating the actuator with an output from the end effector of the robotic surgical system.

In still another embodiment, a method of operating a surgical device with a robotic surgical system includes: engaging an actuator of the surgical device with a first end effector of a first arm of the robotic surgical system; engaging a retainer of the surgical device with an end effector of a second arm of the robotic surgical device; holding at least a portion of the surgical device at least one of rotationally and longitudinally stationary relative to the first end effector of the first arm of the robotic surgical system with the second arm of the robotic surgical system; and actuating the actuator of the surgical device with the first end effector.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 4A is a schematic cross-section of an embodiment of a surgical device including a rotational fastener deployment system prior to being engaged with the end effector of a robotic surgical arm;

FIG. 4B is a schematic cross-section of the surgical device of FIG. 4A engaged with the end effector of the robotic surgical arm;

FIG. 5 is a schematic cross-section of an embodiment of a surgical device including a rotational fastener deployment system;

FIG. 6A is a schematic cross-section of an embodiment of a surgical device including a linear fastener deployment system;

FIG. 6B is a schematic cross-section of the surgical device of FIG. 6A after one actuation cycle;

DETAILED DESCRIPTION

Figure 1A:
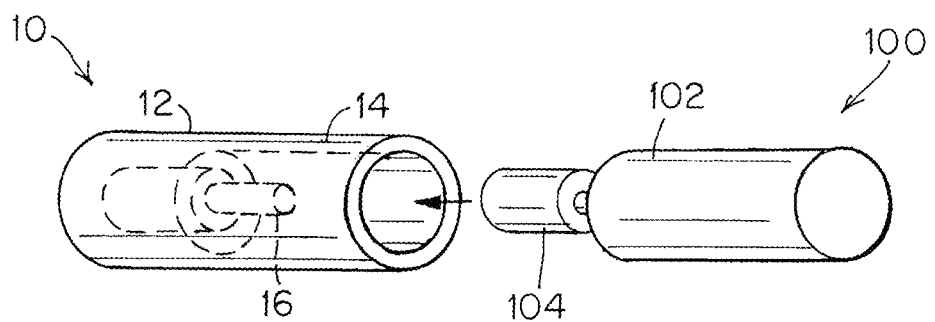
FIG. 1A is a schematic representation of an embodiment of a surgical device.

The Inventors have recognized that robotic surgical systems may be equipped with surgical devices to enable a variety of surgical procedures. However, traditional handheld surgical devices are not adapted to easily interface with robotic surgical systems. Therefore, the Inventors have recognized the benefits associated with surgical devices that are specifically constructed to interface with, and be operated by, the end effectors of one or more robotic surgical arms.

In view of the above, in some embodiments, a surgical device may be constructed to be actuated by a corresponding end effector of an arm of a robotic surgical system. Specifically, the surgical device may include an actuator that is constructed and arranged to be engaged by the end effector of the robotic surgical arm such that an output of the end effector actuates the actuator. Once actuated, the actuator may provide any desired output including, but not limited to linear and/or rotational movement of one or more portions of the surgical device to perform a desired surgical device operation.

Depending on the particular embodiment, it may be desirable to hold at least a portion, including a portion of a housing, of a surgical device rotationally and/or longitudinally stationary relative to one or more arms of a robotic surgical system. In one embodiment, the surgical device may include one or more retainers that are constructed to interface with a portion of a first robotic surgical arm to maintain at least a portion of the surgical device rotationally and/or longitudinally stationary relative to the end effector of the first robotic surgical arm. In other embodiments, the actuator of a surgical device may be engaged with the end effector of a first robotic surgical arm and a portion of the surgical device may be constructed and arranged to be grasped by, or otherwise interfaced with, a second robotic surgical arm. In such an embodiment, the second robotic surgical arm may hold the surgical device stationary relative to the end effector of the first robotic surgical arm. Specific embodiments of each of these concepts are described in more detail below.

In embodiments where a surgical device is held stationary relative to a first robotic surgical arm using a retainer that is selective coupled with the first robotic arm, the coupling may be provided using any desired construction. For example, in one embodiment, a flexible sleeve sized and shaped to form a compression fit with a distal portion of the robotic surgical arm may be used. Alternatively, in other embodiments, a hook, a notch, interlocking mechanical features, or any other suitable feature capable of interacting with a portion of the robotic surgical arm to retain the surgical device thereon during actuation may be used.

In embodiments, where a surgical device is held stationary relative to a first end effector of a first robotic surgical arm by a second end effector of a second robotic surgical arm, the surgical device may be engaged with the second end effector in any appropriate way. Possible constructions include, but are not limited to: protrusions from the surgical device housing; portions of the surgical device with cross sections sized and shaped to be grasped by the second end effector; hooks; notches; interlocking mechanical features; and/or any other feature capable of being engaged with, and retained by, the second end effector to hold the surgical device linearly and/or rotationally stationary relative to the first robotic surgical arm.

An actuator of a surgical device may be constructed to be actuated by any appropriate output from an end effector of a robotic surgical arm. For example, outputs that may be used by an actuator include, but are not limited to rotational motion, linear pushing or pulling, opening or closing of the end effector, electrical current from the end effector, heating from the end effector, and/or any other appropriate type of output from an end effector capable of actuating the actuator of the surgical device. Types of end effectors that may interface with an actuator of a surgical device to provide these types of inputs to an actuator, include, but are not limited to forceps, a needle driver, a laser, retractors, a cautery instrument, an electrical probe, or any other suitable end effector capable of being used with a robotic surgical system. For example, in one such embodiment, the end effector includes forceps of a robotic surgical arm that grasp, push, pull, and/or rotate a corresponding trigger of the actuator. In another embodiment, an electrical current may be output from the end effector to an electric motor disposed in the surgical device to actuate the system. In yet another embodiment, the actuator may include a shape memory alloy that is constructed and arranged to be heated by the end effector to actuate the surgical device. In still another embodiment, the actuator includes a piezoelectric material that produces a linear and/or rotational displacement in response to an electrical current input from the end effector to the piezoelectric material of the surgical device.

In view of the above, it should be apparent that the disclosed surgical devices should not be limited to any particular type of actuator and/or output from an end effector of a robotic surgical arm as the disclosure is not so limited. Additionally, the actuator of a surgical device may either use a single input and/or multiple types of inputs from one or more end effectors of a robotic surgical arm to control either one or multiple functions of the surgical device. For example, electrical current may be used to actuate a first function of a surgical device while linear motion or rotation may be used to actuate a second function of the surgical device. In some embodiments, a surgical device may also include an actuator that alters an output from the surgical device in response to a different degree of an input applied to the actuator. For example, applying a greater force when opening, closing, rotating, pushing, and/or pulling an end effector and/or applying a larger electrical current may increase a force and/or speed of an output from the actuator.

An actuator of a surgical device may provide any desired type of motion, or other output, to perform a desired operation of the surgical device in response to an input from an end effector of a robotic surgical arm. For example, in one embodiment, an actuator may output one or more of rotation, linear motion in one or more directions, heat, or other desired outputs. These outputs from an actuator of a surgical device may be used to actuate any number of different mechanisms including, but not limited to, scissors, suturing devices, surgical fastener deployment devices (e.g. staplers, tackers, coil fastener devices, and other similar fastening systems), biopsy devices, surgical sealant and/or hemostatic agent deployment devices, and/or any other desired operation. In one such embodiment, a rotational and/or linear output from an actuator may be used to rotate and/or distally displace one or more surgical fasteners, including a stack of surgical fasteners, to deploy a distal most surgical fastener from a distal end of the surgical device into tissue, bone, and/or a prosthetic. In another embodiment, a cyclic linear motion may be used to cyclically actuate surgical scissors to cut tissue. In yet another embodiment, a rotational output from an actuator may be used to rotate a needle of the surgical device for suturing. Of course it should be understood that a surgical device may be used to perform any number of desired surgical functions, and that the current disclose should not be limited to only those specific applications described herein.

In one embodiment, an actuator of a surgical device may include one or more transmission components that may be constructed to transmit and/or convert motion output from an end effector of a robotic surgical arm into a desired output motion. Appropriate transmission components include, but are not limited to, linkages, gears, cables, shafts, camming arrangements, springs, combinations of the above, and/or any other component capable of transmitting a desired motion and/or force.

In embodiments where it is undesirable to provide a reciprocating output from a surgical device, such as when it is desirable to avoid back driving of surgical fasteners, one or more transmission components of an actuator may provide unidirectional actuation of the system. This may permit motion of the end effector of a robotic surgical arm to be cyclically repeated without reversing an output from the surgical device. For example, an end effector of a robotic surgical arm may be cyclically moved in a longitudinal and/or rotational direction between first and second positions while it is engaged with the actuator of a surgical device. The end effector may actuate the actuator when it is moved from the first to the second position, but does not actuate the actuator when it is moved in the reverse direction from the second position to the first position. Appropriate unidirectional transmission components that may be used in an actuator include, but are not limited to, a gear clutch, ratchet and pawl mechanisms, walking beam arrangements, directionally biased compliant mechanisms such as elastically deformable non-symmetric ridges, center punch type mechanisms consisting of a punch, a tumbler, and a hammer, combinations of the above, and/or any other appropriate transmission component capable of preventing actuation of a surgical device in one or more directions.

Depending on the particular application, it may be desirable to either increase or decrease a magnitude of an output force and/or displacement from an actuator of a surgical device relative to an input from an associated end effector of a robotic surgical arm. For example, it may be desirable to provide a larger rotational displacement and/or torque from an actuator relative to the rotation of an end effector of a robotic surgical arm. Accordingly, a transmission of an actuator of a surgical device may include a mechanical advantage through the use of appropriate gear ratios, linkage arrangements, or other appropriate components to either increase or decrease an output motion, torque, and/or force relative to an input motion, torque, and/or force from the end effector of the robotic surgical arm.

The surgical devices described herein may be made out of any desirable material or combination of materials. However, in some instances, the surgical devices described herein may be made from materials that are either sterilized and/or are sterilizable using any appropriate method including, but not limited to, heat, radiation, and/or pressure.

In instances where a surgical device includes an outer elongated tubular member, such as an outer cylinder, and/or an inner channel, a central longitudinal axis extending down the length of the tubular member or channel may be parallel to an axis of rotation of an actuator and/or linear movement of the actuator.

As used herein, the term "distal direction" within a surgical device may refer to a direction that extends along a central longitudinal axis of the surgical device towards a distal end of the surgical device where a desired operation is performed. Correspondingly, a "proximal direction" may refer to a direction that is directed in an opposite direction relative to the distal direction such that it may be directed along the central longitudinal axis of the surgical device away from the surgical device's distal end where the desired operation is performed.

For the sake of clarity the embodiments described below in reference to the figures are described for use relative to a particular way of interfacing with a robotic surgical arm, and/or are shown generically. However, it should be understood that the various surgical devices and actuators described herein may be held stationary relative to a robotic surgical arm in any desired way and may accept any desired type of input as the disclosure is not limited to only the specific embodiments described herein relative to the figures.

Turning to the figures, several non-limiting embodiments are described in further detail. It should be understood that the various systems, components, features, and methods described relative to these embodiments may be used either individually and/or in any desired combination as the disclosure is not limited to only the specific embodiments described herein.

Figure 1B:
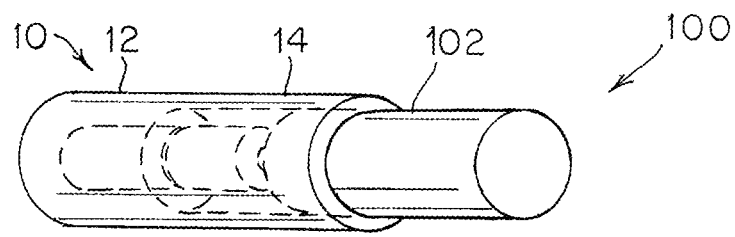
FIG. 1B is a schematic representation of the surgical device of FIG. 1A engaged with an end effector of a robotic surgical arm.
Figure 2A:
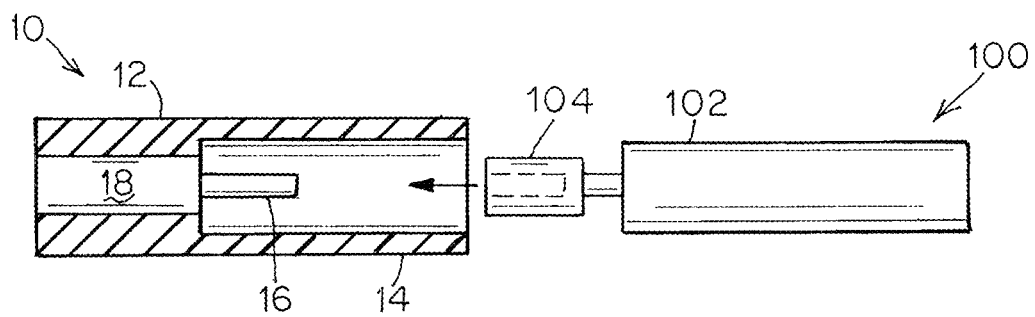
FIG. 2A is a schematic cross-section of the surgical device shown in FIG. 1A.
Figure 2B:
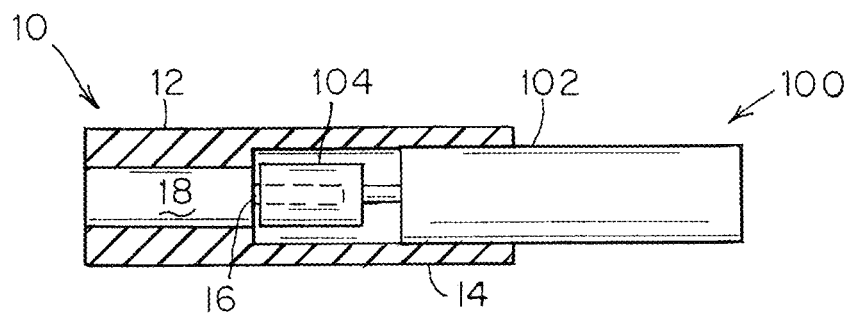
FIG. 2B is a schematic cross-section of the surgical device shown in FIG. 1B engaged with an end effector of a robotic surgical arm.

FIG. 1A depicts an embodiment of a surgical device 10 and a robotic surgical system 100. The surgical device includes a housing 12. The surgical device also includes a trigger 16 and an associated actuator 18 used to actuated an operation of the surgical device, both of which may be disposed within the housing. The surgical device also includes at least one retainer 14 constructed to retain the surgical device on a distal portion of an arm 102 of the robotic surgical system during actuation. In some embodiments, the retainer may maintain the surgical device rotationally and/or longitudinally stationary relative to an end effector 104 and/or longitudinal axis of the arm during actuation. For example, in the depicted embodiment, the retainer corresponds to a compliant sleeve formed from rubber or another suitable compliant material. The compliant sleeve is sized and shaped such that it forms a compression fit with an outer surface of the robotic surgical arm 102. In one such embodiment, an outer transverse dimension, e.g. diameter, of the arm may be larger than an inner transverse dimension, e.g. diameter, of the sleeve. Thus, the robotic surgical arm may be inserted into the compliant sleeve as shown in FIGS. 1B and 2B, and the resulting compression fit retains the surgical device on the robotic surgical arm. However, the current disclosure is not limited to the use of compliant sleeves to retain a surgical device on a robotic surgical arm. For example, in other embodiments, the retainer 14 may comprise a hook, a notch, interlocking mechanical features, or any other suitable feature capable of interacting with a portion of the robotic surgical arm to retain the surgical device thereon during actuation.

The robotic surgical system 100 includes an end effector 104, which in this case corresponds to forceps, located at a distal end of the arm. Accordingly, when the robotic surgical arm is moved into engagement with a surgical device 10, the end effector may be correspondingly engaged with a trigger 16 of an actuator 18 of the surgical device to permit the robotic surgical system to actuate the surgical device. For example, as depicted in the figure, the trigger of the actuator corresponds to a protrusion that extends in a proximal direction within the housing and is accessible through an opening located on a proximal side of the housing 12. The protrusion may be sized and shaped such that the end effector 104 may extend through the opening and grasp the protrusion, or other appropriate trigger or interface. For example, the trigger may include one or more flats that are sized and shaped such that they may be easily grasped and retained by the end effector. In either case, the end effector may then apply any desired input to the trigger including, in this particular embodiment, rotation and/or linear movement about a longitudinal axis of the surgical device. The trigger of the actuator then transmits the input to the actuator 18 to produce a desired output that actuates the surgical device 10. Depending on the embodiment, this transmission of the input to the actuator may either occur through a direct transmission, as in the case of a shaft or cable, or the actuator may include a transmission that either transforms the input to a different type of output, applies a mechanical advantage, and/or provides unidirectional actuation of the surgical device.

While the above embodiment depicts a protrusion used as a trigger for an actuator, a surgical device may include any appropriate type of interface capable of triggering actuation as the disclosure is not so limited. For example appropriate types of features that may interface with an end effector of a robotic surgical system include, but are not limited to: depressions sized and shaped to receive a portion of an end effector (e.g. a hex key, cross, slot, or any other suitable shape), flat protrusions, hooks, loops, cables, electrodes, thermal contact pads, or any other appropriate component capable of being engaged with the end effector and accepting a desired input from the end effector for actuating the surgical device.

Having described the various components of the surgical device of FIGS. 1A-2B, a method of operating the surgical device is described relative to the figures. As depicted in the figures, the end effector 104 located at a distal end of a robotic surgical arm 102 may be inserted into a proximal end of a surgical device 10 as indicated by the arrow. As the end effector 104 is inserted into the surgical device, a retainer 14 of the surgical device engages with and retains a portion of the arm to secure the surgical device 10 to a distal end of the arm. Either prior to, during, or after the retainer is engaged, the end effector of the robotic arm is also engaged with a trigger 16 of the surgical device, which in the depicted embodiment corresponds to forceps grasping a protrusion extending proximally toward the end effector. An actuator 18 of the surgical device is then actuated by an output from the end effector of the robotic surgical system that is applied to the trigger. The actuator may then actuate one or more components within the surgical device to perform a desired operation.

Figure 3A:
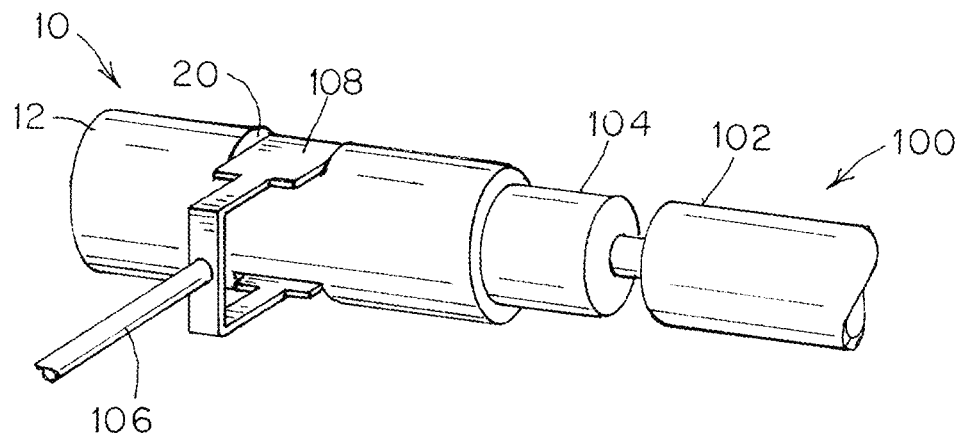
FIG. 3A is a schematic representation of an embodiment of a surgical device held stationary relative to a first end effector of a first robotic surgical arm by a second end effector of a second robotic surgical arm.

FIG. 3A shows another embodiment of a surgical device 10. In the depicted embodiment, the surgical device is engaged with both a first robotic surgical arm 102 and a second robotic surgical arm 106 of a robotic surgical system 100. Similar to the above embodiment described relative to FIGS. 1A-2B, a first end effector 104 of the first arm is inserted into a proximal end of a housing 12 of the surgical device to provide an input to an actuator of the surgical device. At the same time, at least a portion 20 of the surgical device is constructed and arranged to be retained by a second end effector 108 of the second arm 106 of the robotic surgical system. Thus, the second arm 106 may hold at least a portion of the surgical device either rotationally and/or longitudinally stationary relative to a longitudinal axis of the first arm and/or first end effector. By holding the surgical device stationary relative to the first arm and/or first end effector, the first end effector may apply a desired input to an actuator of the surgical device as previously described above.

As shown in the figures, in some embodiments, a portion 20 of the surgical device's housing that interfaces with the second end effector 108 to retain the surgical device 10 may correspond to a portion of the housing 12 that is sized and shaped to be engaged with, and retained by, opposing portions of a pair of forceps. This portion of the housing may also include a cross-sectional shape that is easily engaged with and retained by the second end effector, for example, the cross-sectional shape may include a reduced cross section with two flats, or any other appropriate shape capable of being engaged by the end effector, that are located on opposing sides of the cross-sectional shape of the surgical device housing. However, in other embodiments, the portion of the housing engaged by the end effector may include one or more of the following features: a protrusion from the housing; curved surfaces; textured surfaces; magnetic materials; hooks; mechanically interlocking features; and/or any other appropriate feature capable of being engaged with and retained by the second end effector.

Figure 3B:
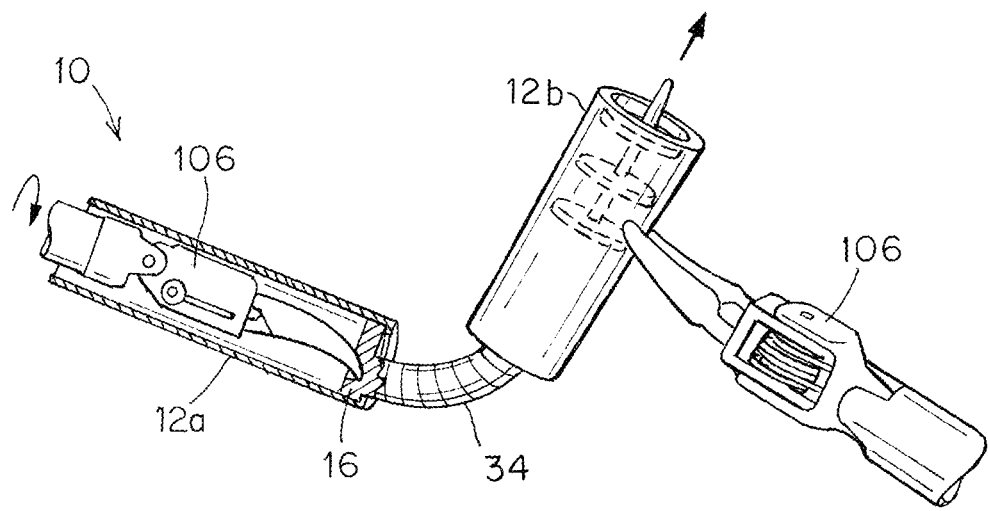
FIG. 3B is a schematic representation of an embodiment of a surgical device including a flexible transmission disposed between first and second housing portions.

In some embodiments, it may be desirable to permit at least some movement between a portion of a surgical device where an end effector applies an input to the device and a portion of the surgical device where an operation is performed. FIG. 3B depicts one such embodiment of a surgical device 10. In the depicted embodiment, a flexible transmission 34 couples a first housing portion 12a of the surgical device to a second housing portion 12b of the surgical device. The first housing portion includes the portion of the surgical device constructed and arranged to be secured by a second end effector 106 of the second arm and includes the components of the surgical device that perform a desired operation at a distal end of the device. The second housing portion may separately include a trigger 16 of the actuator that similar to the above embodiments is constructed and arranged to interface with the first end effector 104 of the first arm. The flexible transmission may correspond to any appropriate constructions including but not limited to cables, flexible interconnected links, and flexible shafts to name a few. Thus, the flexible transmission may transmit rotational and/or linear motion between the two housings portions for use in actuating the surgical device.

FIGS. 4A-4B show a cross-sectional view of an embodiment of a surgical device 10 that functions as a fastener deployment system that includes a stack of one or more surgical fasteners 30 disposed on a rotationally stationary threaded mandrel 24 located within the device. In the depicted embodiment, surgical fasteners include a threaded through hole and/or coil body that are engaged with the threading of the mandrel. Additionally, a cross section of the head perpendicular to a longitudinal axis of the surgical device complements an internal non-circular cross-section of a rotator 26 of the surgical device. The rotator may correspond to an elongated tubular member that is rotatable about a longitudinal axis of the surgical device and/or surgical fasteners. Additionally, the rotator is operatively connected to the trigger through one or more transmission components and/or unidirectional transmission component, such as gear clutch 22 that is operatively connected to the trigger. Thus, rotation of the trigger in a first direction will rotate the rotator while rotation of the trigger in a second opposing direction does not which enables unidirectional rotation of the rotator. Due to the threading of the fasteners engaged with the threaded mandrel, rotating the fasteners applies a distally directed force to the surgical fasteners and displaces the fasteners in a distal direction. As the fasteners are displaced in a distal direction, a distal most fastener is displaced out of the distal end of the surgical device and into an underlying prosthetic, bone, muscle, and/or tissue.

During operation, an end effector 104 of an arm 102 of a robotic surgical system 100 is inserted into the surgical device 10 where it engages a trigger 16 of an actuator of the device. For example, the end effector may correspond to forceps that grasp a protrusion corresponding to the trigger. Similar to the previously described embodiments, the surgical device may be held rotationally and longitudinally stationary relative to the arm 102 using any number of different arrangements. Once engaged with the trigger, the robotic surgical system 100 may actuate the end effector 104 to provide a desired input to the trigger 16, which in this embodiment corresponds to cyclic rotation of the end effector between a first position and a second position as indicated by the arrows. The gear clutch 22 of the actuator correspondingly rotates the rotator in a desired direction in response to movement of the trigger in the first direction and maintains the rotator stationary when the trigger is rotated in the opposing second direction. This rotation of the rotator and surgical fasteners in a desired direction results in the surgical fasteners moving in a distal direction where they are deployed from a distal end of the surgical device.

While the above embodiment is directed to an application that only permits a rotational output of the surgical device in one direction, embodiments in which a cyclical output is output from an actuator of a surgical device are also contemplated as the disclosure is not so limited. Additionally, it should be understood that the depicted gear clutch may be combined with any number of different components to provide the desired unidirectional actuation and/or to provide a desired mechanical advantage as previously described.

FIG. 5 shows an embodiment similar to that depicted in FIGS. 4A-4B. In this embodiment, a surgical device 10 includes one or more surgical fasteners 30 disposed in the surgical device that may be deployed into prosthetic material, bone, muscle, and/or tissue. The surgical device 110 may also include an actuator with a trigger 16 and gear clutch 22 as previously described. However, the surgical fasteners include one or more external threads that are engaged with one or more internal threads 32 provided on an interior channel of the surgical device surrounding the one or more surgical fasteners. For example, the internal threads may be formed on an interior surface of an elongated tubular member forming a housing of the surgical device. Correspondingly, the surgical device includes a shaft 28 that is operatively connected to the trigger 16 through the gear clutch 22 or other transmission component. The shaft 28 may have a non-circular cross section and is sized and shaped to fit within a correspondingly sized and shaped through hole and/or channel formed through the surgical fastener. Thus, the surgical fasteners may be rotated relative to the internal threads of the surgical device in response to rotation of the shaft about its longitudinal axis.

In the above embodiment, an end effector, not depicted, may rotate the trigger 16 in a first direction. In response to this rotational input, the gear clutch 22 of the actuator may rotate the shaft 28, and correspondingly, the one or more surgical fasteners 30, relative to the internal threads 32 of the surgical device. As the one or more surgical fasteners are rotated relative to the internal threads, the threads apply a reactive thrust to the fastener 112, causing the fastener 112 to be driven in a distal direction along the length of the shaft 116, out of the surgical device 110 and into the prosthetic material, bone, muscle, and/or tissue. In contrast, when the end effector is rotated in a second opposite direction, the shaft 28 may be held stationary preventing back driving of the one or more surgical fasteners.

In another embodiment, an actuator of a surgical device may output linear motion to perform a desired operation. For example, FIGS. 6A-6B depict a surgical device that is linearly actuated to deploy one or more linearly deployed surgical fasteners 214 (e.g. tacks and/or staples) from the device. In the depicted embodiment, the surgical device 200 includes an actuator 202 that includes a trigger 204 and a linear rack and pawl arrangement including a pawl arm 206 and rack arm 208 to prevent backwards movement of the actuator. During actuation, an end effector of a robotic surgical arm may apply a linear input to the trigger to linearly reciprocate the trigger between a proximal and distal direction. As the trigger is moved distally the pawl arm is moved distally. A pawl 206a, such as a distally extending tab, is located on a distal end of the pawl arm and is engaged with a slot 208a, or other feature, located on the rack arm. Therefore, the pawl applies a distally directed force to the slot it is engaged with to move the rack arm in the distal direction as well. A distal end of the rack arm may be in contact with a proximally located fastener. Thus, the distal extension of the rack arm displaces the stack of surgical fasteners, and at least a distal most surgical fastener, in a distal direction along the length of the shaft, out of a distal end of the surgical device, and into a prosthetic material, bone, muscle, and/or tissue. In some embodiments, the force applied to one or more surgical fasteners is sufficient to overcome a restraining force applied to at least a distal most fastener by a one or more optional restraining tabs 216 to prevent unintentional distal displacement of the one or more surgical fasteners.

In some application it may be desirable to prevent proximal movement of the stack of surgical fasteners and a portion of the actuator in contact with the surgical fasteners. For example, as the pawl arm 206 is moved in a proximal direction, movement of the surgical fasteners 214 and the rack arm in the proximal direction may be prevented by a ratchet and pawl mechanism formed between the rack arm and an interior of the surgical device. Specifically, teeth 210 may be disposed on an interior surface of the surgical device 200 and a second pawl 212 may be connected to the rack arm 208 in a way that interacts with the teeth to prevent proximal motion of the rack arm in the proximal direction. Thus, when the trigger 204 is withdrawn in the proximal direction, the pawl 206a is cammed up and out of the slot 208a it is engaged with and into the next most proximal slot formed on the rack arm. This actuation sequence may be continued to sequentially displace the rack arm, and corresponding surgical fasteners, in a distal direction one fastener length at a time to deploy the surgical fasteners from a distal end of the device.

While the rack arm of the rack and pawl arrangement has been depicted as contacting the surgical fasteners, embodiments in which the pawl arm is constructed and arranged to be contact the surgical fasteners and be displaced distally down a length of a surgical device are also contemplated. Additionally, in some embodiments, the relative positioning of the teeth and pawl used to prevent proximal movement of the actuator may also be reversed as the disclosure is not so limited.

Figure 7:
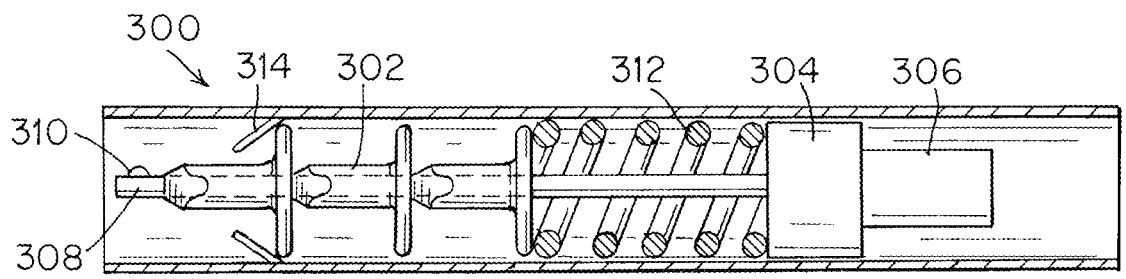
FIG. 7 is a schematic cross-section of an embodiment of a surgical device including a linear fastener deployment system with a spring to bias a stack of tacks towards a distal end of the surgical device.

FIG. 7 shows another embodiment of a surgical device 300 that deploys one or more surgical fasteners 302 using reciprocating linear actuation. The fasteners 302 may be slidably supported, or otherwise disposed on, a fastener carrier 308. In the depicted embodiment the fastener carrier corresponds to an elongated shaft that extends axially from a proximal portion of the surgical device towards a distal end of the surgical device through one or more through holes formed in the surgical fasteners disposed thereon. A distal portion or end of the anchor carrier may include a coupling 310, such as a protrusion or mechanically interlocking feature, that is constructed and arranged to releasably engage with a distal most fastener. A proximal end of the anchor carrier may be operatively connected to an actuator 304 of the surgical device that includes a trigger 306 that may be actuated using any desired input to linearly reciprocate the anchor carrier between a first proximal position and a second distal position where a distal end of the anchor charrier extends out from the surgical device. The surgical device also includes one or more retaining tabs that apply a distally directed force to a distal most surgical fastener to prevent distal movement of the surgical device until the surgical device is actuated.

In some embodiments, the surgical device of FIG. 7 may also include a compressed spring 312, or other appropriate type of follower, capable of applying a distally directed force to the stack of one or more surgical fasteners. This distally directed force may displace the one or more surgical fasteners towards a distal end of the surgical device and a deployment position for a distal most surgical fastener. Accordingly, as surgical fasteners are deployed from the surgical device, the spring may expand by a surgical fastener length to displace the stack of surgical fasteners by a surgical fastener length in the distal direction. Appropriate types of springs include, but are not limited to, a coil spring, a conical spring, a pneumatic spring, an appropriately shaped component made of a compressible material (e.g. rubber), or any other appropriately shaped and sized compressible component capable of applying a force to the fasteners when it is compressed. Other arrangements capable of displacing a stack of surgical fasteners that may also be used include, for example, walking beam arrangements, rack and pawl arrangements, tabs, combinations of the above, and/or any other arrangement capable of displacing a stack of fasteners in a desired direction. The device may also include one or more restraining tabs 314 that extend inwards and distally to apply a restraining force to a distal most fastener to keep the fastener from being inadvertently displaced out of a distal end of the device.

During use, an end effector of a robotic surgical fastener, not depicted, may apply a desired input to a trigger 306 of an actuator 304 of the surgical device 300. For example, the end effector may apply a linear distally directed force to the trigger that displaces the anchor carrier of the surgical device in a distal direction. The anchor carrier correspondingly applies the distally directed force to a distal most surgical fastener 302 via a selective connection made between the coupling 310 of the anchor carrier and the surgical fastener. The distally directed force is sufficient to overcome a proximally directed restraining force applied to the distal most surgical fastener by the restraining tabs 314 to displace the distal most surgical fastener and into a desired prosthetic material, bone, muscle, and/or tissue. As the distal most fastener is deployed, the spring 312 may expand during deployment of the distal most surgical fastener to move the stack of surgical fasteners in a distal direction.

After deploying a surgical fastener, the end effector may apply a proximal force to the trigger 306 of the surgical device 300 which withdraws the fastener carrier 308 in a proximal direction. Alternatively, the surgical device may be biased back to the unactuated position by a spring or other similar component. In either case, the surgical fastener may be retained within the substrate it is deployed into by barbs or other features such that the proximal movement of the fastener carrier disengages the coupling 310 from the deployed surgical fastener and withdraws the carrier from within the deployed fastener. The fastener carrier may be continued to be withdrawn proximally until the coupling engages with the next distal most fastener. The described actuation sequence may then be repeated to deploy the remaining surgical fasteners.

Figure 8A:
FIG. 8A is a schematic representation of an embodiment of a surgical device including a helical guide track.
Figure 8B:
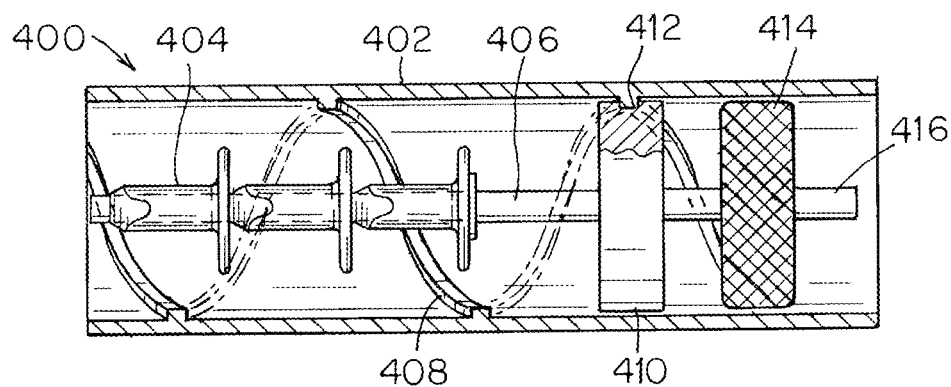
FIG. 8B is a schematic cross-section of the surgical device of FIG. 8A.

FIGS. 8A-8B depict an embodiment of a surgical device 400 configured to transform a rotational input from an end effector of a robotic surgical system into linear motion. The surgical device includes a housing 402, which in the depicted embodiment is an outer cylindrical housing. One or more surgical fasteners 404 are slidably disposed on a rotatable shaft 406 that extends distally through an inner channel of the surgical device. The housing, or a component disposed within the housing, may have an inner surface with a spiral track 408 formed thereon that extends along at least a portion of the length of the housing. FIG. 8B shows a cross-section of the surgical device, with a displacement block 410 coupled to the guide track by a coupling such as a threaded groove, a bearing, or other similar component capable of engaging the guide track. The displacement block is also slidably disposed on the shaft, but is held rotationally stationary relative to the shaft. Such a coupling between the displacement block and shaft may be provided by a shaft with a non-circular cross section and a correspondingly shaped and sized through hole formed in the displacement block that the shaft passes through. In at least one embodiment, the shaft 420 is coupled to a gear clutch, ratchet and pawl mechanism, or other unidirectional coupling 414 used to transmit rotational motion applied to a trigger 416 by an end effector of a robotic surgical arm to the rotatable shaft. Accordingly, the shaft may be rotated in one direction relative to the surgical device housing which correspondingly rotates the displacement block relative to the guide track to displace the displacement block in a distal direction through the surgical device. As the displacement block is moved distally, the displacement block applies a distally directed force to the one or more surgical fasteners to deploy the one or more surgical fasteners from a distal end of the surgical device.

While the above embodiment has been described as including a guide track formed on the housing and a corresponding groove, or similar feature, formed on the displacement block, the locations of these features may be reversed as the disclosure is not limited to the particular arrangement and construction depicted in the figures.

Figure 9:
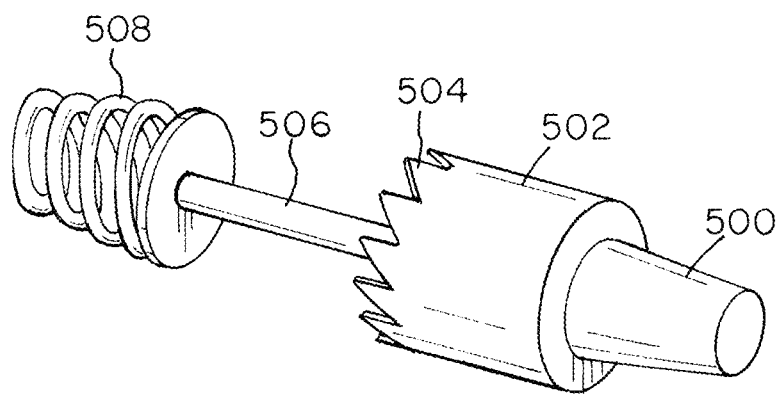
FIG. 9 is a schematic representation of a linear actuator including a rotatable camming actuator.

FIG. 9 shows another embodiment of an actuator for use with a surgical device. The actuator includes a rotatable camming actuator 502 that creates linear movement in response to linear inputs, similar to the actuation mechanism of a retractable ball point pen. During use, an end effector of a first arm of a robotic surgical system, not depicted, may engage and actuate a linearly displacable trigger 500, which in the depicted embodiment is a push button. Depression of the trigger distally displaces the rotatable camming actuator 502. In one embodiment, the rotatable camming actuator 502 has teeth 504 that engage features on a corresponding actuator, not shown, which may drive a stepwise rotation of a shaft 506. In some embodiments, a compressible spring 508 is located on a distal end of the shaft. The depicted actuator may be included in any surgical device that uses a linear actuation input to perform a desired operation.

Figure 10:
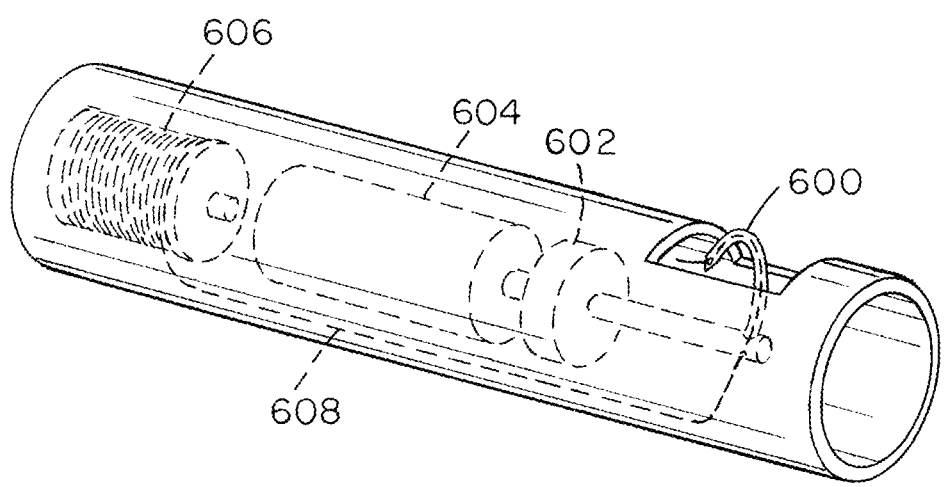
FIG. 10 is a schematic depiction of an embodiment of a surgical device including a rotating needle.

FIG. 10 shows an embodiment of a surgical device that includes a rotating needle 600 and a bobbin 606 that unspools suture thread 608 to the rotating needle 612. In one embodiment, the bobbin 614 freely rotates to unspool thread as the needle is rotated. In such an embodiment, an end effector actuates the device using an input to a motor 604, or any appropriate actuator capable of outputting a rotational motion, including the actuators described above relative to the other disclosed embodiments. The surgical device may include a transmission with a gear clutch 602 that transmits a rotational motion to the needle. As the needle is rotated it may deploy sutures into a prosthetic material, muscle, and/or tissue.

Figure 11:
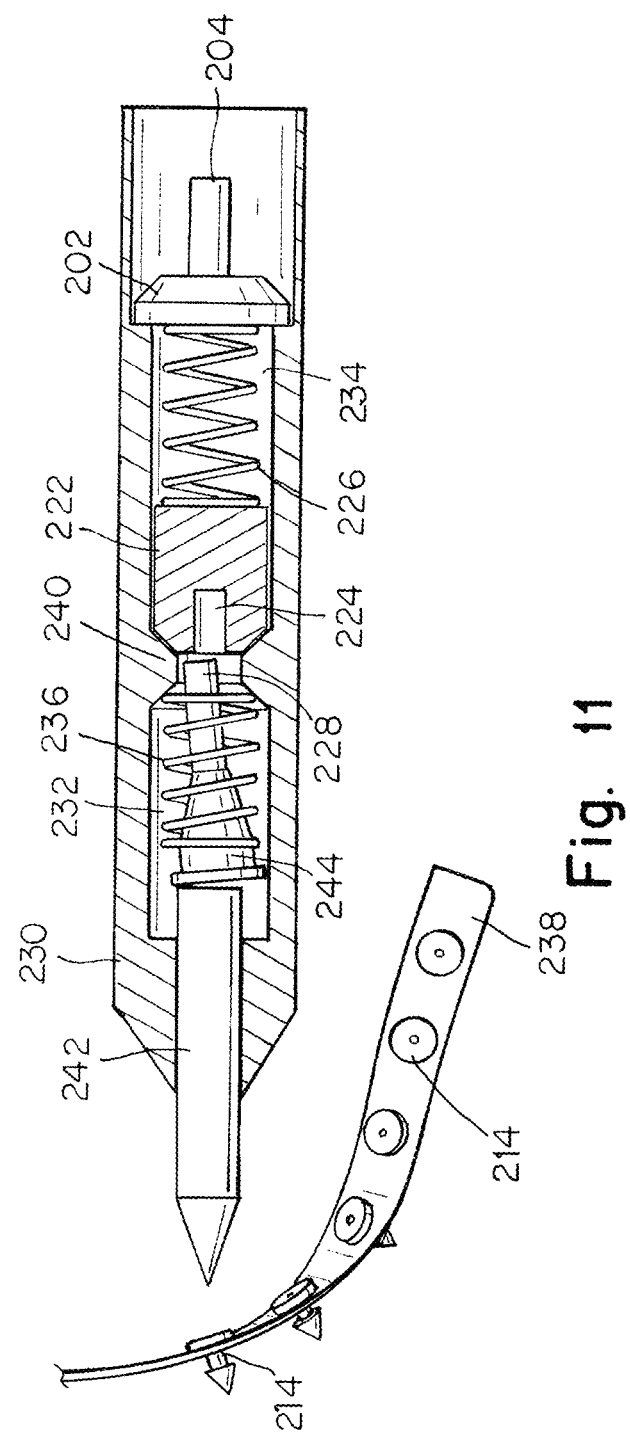
FIG. 11 is a schematic cross-section of a surgical device including a linear fastener deployment system with a center punch type mechanism.

FIG. 11 depicts another embodiment in which an actuator of a surgical device outputs linear motion to actuate a punch to deploy one or more linearly deployed surgical fasteners 214. In the depicted embodiment, the surgical device includes an actuator 202 with a trigger 204 that actuates a center punch type mechanism. The punch may include a housing 230 with a first chamber 232 and a second chamber 234 that may be separated by a tapered portion 240. The first chamber retains a hammer 222 with a blind hole 224 formed in the center of a distal end of the hammer 222 and a first spring 226 that biases the hammer 222 in the distal direction. In one embodiment, the second chamber 234 retains a punch 242, which may include a pointed distal end, and a second spring 236 with a tumbler 244 associated with the second spring. In one embodiment, the tumbler is tapered with a shape that at least partially conforms to a shape of the tapered portion 240. Additionally, the tumbler may have a rod 228 that extends proximaly from a proximal end of the tumbler, and that may be sized and shaped to pass through the tapered portion 240 and into the blind hole 224 of the hammer. As will be appreciated, the tapered portion 240 retains the first spring, the second spring, the tumbler, and the hammer at least partially within their respective chambers. In one embodiment, a ribbon 238 with one or more fasteners 214 may be provided outside the housing.

During actuation, an end effector of a robotic surgical arm may apply linear input to the trigger 204 to linearly reciprocate the trigger 204. In some embodiments, the trigger and a portion of the housing containing the punch may be moved distally relative to another portion of the surgical device. Alternatively, in other embodiments, the trigger may simply correspond to a portion of the device held stationary relative to the robotic surgical device, and the entire surgical device may be moved axially to actuate the surgical device. Specifically, in an initial state, the rod 228 of the tumbler 244 may be angled such that the rod 228 contacts a distal end of the hammer 222 such that it is offset from the blind hole 224. As the trigger moves the housing distally, the punch 242 presses the rod of the tumbler against the distal end of the hammer, causing the first and second springs to compress. Further distal movement of the housing causes the tapered portion 240 of the housing to cam against the tapered portion of tumbler 244, which pushes the rod of the tumbler into alignment with the blind hole of the hammer. Once the rod of the tumbler is aligned with the blind hole, the hammer is accelerated in the distal direction by the expansion of the first spring. The hammer then impacts the rod to apply a distally directed impulse through the tumbler to the punch. This impulse results in the punch applying a distally directed force to whatever surface it is in contact with, including as illustrated in the figure, a head of a fastener 214 it is placed in contact with.

Although the above described embodiments have been directed to surgical devices that deploy surgical fasteners, other types of functionalities are also contemplated. For example, other types of surgical materials and systems may be delivered include adhesives, meshes, plaster, medical compounds, surgical sealants and hemostatic agents, and/or any other appropriate material that may be desirable to be delivered using the disclosed surgical devices. In another embodiment, the actuation outputs of a surgical device may be used to actuate a tool such as various cutting implement including but not limited to, scissors, drills, rongeur, and biopsy probes. Accordingly, it should be understood that the disclosed surgical devices may incorporate any desirable actuatable system capable of being used by a robotic surgical system.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A surgical device for use with a robotic surgical system, the surgical device comprising:
   a housing having a proximal portion and a distal portion;
   an actuator adapted to mechanically interface with an end effector of an arm of the robotic surgical system such that a mechanical output from the end effector of the arm of the robotic surgical system actuates the actuator, wherein the actuator is supported by the housing; and
   a compliant sleeve coupled to the proximal portion of the housing and configured to receive and retain a distal portion of the arm of the robotic surgical system inside of the sleeve during actuation of the actuator, wherein the sleeve is configured to form a compression fit with the distal portion of the arm received inside of the sleeve, and wherein the sleeve is configured to maintain the housing and the actuator rotationally and longitudinally stationary relative to the distal portion of the arm.

2. The surgical device of claim 1, wherein the surgical device includes one or more surgical fasteners, and wherein actuation of the actuator deploys the one or more surgical fasteners from a distal end of the surgical device.

3. The surgical device of claim 1, further comprising the arm, wherein the sleeve is sized and shaped to be elastically deformed around the distal portion of the arm.

4. The surgical device of claim 1, wherein an output of the actuator outputs linear movement.

5. The surgical device of claim 1, wherein an output of the actuator outputs rotational movement.

6. The surgical device of claim 1, wherein the surgical device has an external diameter smaller than 5 mm.

7. The surgical device of claim 1, wherein the actuator is configured to be actuated by at least one of rotational motion of the end effector, linear pushing of the end effector, linear pulling of the end effector, opening of the end effector, closing of the end effector, and heating from the end effector.

8. The surgical device of claim 1, wherein the sleeve is configured to engage the distal portion of the arm located proximal to the end effector.

9. The surgical device of claim 1, wherein the sleeve is configured to releasably receive and retain the distal portion of the arm.

10. The surgical device of claim 1, wherein the end effector and the distal portion of the arm are maintained within the compliant sleeve, and wherein the actuator is actuated by linear pushing of the end effector or linear pulling of the end effector relative to the actuator while the housing and the actuator are maintained rotationally and longitudinally stationary relative to the distal portion of the arm.

11. The surgical device of claim 10, wherein the linear pushing of the end effector or linear pulling of the end effector comprises linear pushing or linear pulling along a longitudinal axis of the arm.

12. The surgical device of claim 1, wherein the sleeve is configured such that the end effector of the arm does not contact the sleeve when the surgical device is disposed on the arm.

13. A robotic surgical system, comprising:
an arm having a distal portion;
an end effector disposed on the distal portion of the arm; and
a surgical device comprising:
 a housing having a proximal portion and a distal portion;
 an actuator adapted to mechanically interface with the end effector such that a mechanical output from the end effector of the arm of the robotic surgical system actuates the actuator, wherein the actuator is supported by the housing; and
 a compliant sleeve operatively coupled to the housing, wherein the distal portion of the arm is received in an inside of the sleeve to retain the housing on the distal portion of the arm of the robotic surgical system with the end effector engaged with the actuator, and
wherein the sleeve forms a compression fit with the distal portion of the arm received inside of the sleeve, and wherein the sleeve is configured to maintain the housing and the actuator rotationally and longitudinally stationary relative to the distal portion of the arm.

14. The surgical system of claim 13, wherein the end effector is disposed at least partially within the housing.

15. The surgical system of claim 13, wherein the surgical device includes one or more surgical fasteners, and wherein actuation of the actuator deploys the one or more surgical fasteners from a distal end of the housing.

16. The surgical system of claim 13, wherein the sleeve is sized and shaped to be elastically deformed around the distal portion of the arm.

17. The surgical system of claim 13, wherein an output of the actuator outputs linear movement.

18. The surgical system of claim 13, wherein an output of the actuator outputs rotational movement.

19. The surgical system of claim 13, wherein the surgical device has an external diameter smaller than 5 mm.

20. The surgical system of claim 13, wherein the actuator is actuated by at least one of rotational motion of the end effector, linear pushing of the end effector, linear pulling of the end effector, opening of the end effector, closing of the end effector, electrical current from the end effector, and heating from the end effector.

21. The surgical system of claim 13, wherein the sleeve comprises rubber.

22. The surgical system of claim 13, wherein the sleeve has a maximum inner transverse dimension less than a minimum outer transverse dimension of the distal portion of the arm.

23. The surgical system of claim 13, wherein the end effector comprises forceps.

24. The surgical system of claim 13, wherein the end effector is mechanically interfaced with the actuator via at least one selected from the group of a hex key, cross, and slot.

25. The surgical system of claim 13, wherein the sleeve is engaged with the distal portion of the arm located proximal to the end effector.

26. The surgical device of claim 13, wherein the sleeve is configured to releasably receive and retain the distal portion of the arm.

27. The surgical device of claim 13, wherein the end effector and the distal portion of the arm are maintained within the compliant sleeve, and wherein the actuator is actuated by linear pushing of the end effector or linear pulling of the end effector relative to the actuator while the housing and the actuator are maintained rotationally and longitudinally stationary relative to the distal portion of the arm.

28. The surgical device of claim 27, wherein the linear pushing of the end effector or linear pulling of the end effector comprises linear pushing or linear pulling along a longitudinal axis of the arm.

29. The surgical device of claim 13, wherein the sleeve is configured such that the end effector of the arm does not contact the sleeve when the surgical device is disposed on the arm.

30. A surgical device for use with a robotic surgical system, the surgical device comprising:
 a housing having a proximal portion and a distal portion;
 an actuator adapted to mechanically interface with an end effector of an arm of the robotic surgical system such that a mechanical output from the end effector of the arm of the robotic surgical system actuates the actuator, wherein the actuator is supported by the housing, and wherein the actuator includes a transmission configured to provide unidirectional actuation of the actuator; and
 a compliant sleeve coupled to the proximal portion of the housing and configured to receive and retain a distal portion of the arm of the robotic surgical system inside of the sleeve during actuation of the actuator, wherein the sleeve is configured to form a compression fit with the distal portion of the arm received inside of the sleeve.

31. The surgical device of claim 30, wherein the sleeve is configured such that the end effector of the arm does not contact the sleeve when the surgical device is disposed on the arm.

32. The surgical device of claim 30, wherein the actuator is configured to be actuated by rotational motion of the end effector.

33. The surgical device of claim 32, wherein the rotational motion of the end effector comprises rotational motion about a longitudinal axis of the arm.

34. The surgical device of claim 30, wherein the sleeve is configured to releasably receive and retain the distal portion of the arm.

35. The surgical device of claim 30, wherein the actuator is actuated by linear pushing of the end effector or linear pulling of the end effector.

36. The surgical device of claim 35, wherein the linear pushing of the end effector or linear pulling of the end effector comprises linear pushing or linear pulling along a longitudinal axis of the arm.

37. The surgical device of claim 30, wherein the end effector actuates the actuator when the end effector moves from a first position to a second position and does not actuate the actuator when the end effector moves from the second position to the first position.

* * * * *